United States Patent
Murad

(10) Patent No.: US 6,358,539 B1
(45) Date of Patent: Mar. 19, 2002

(54) PHARMACEUTICAL COMPOSITIONS FOR REDUCING THE APPEARANCE OF CELLULITE

(76) Inventor: Howard Murad, 4265 Marina City Dr., Marina del Rey, CA (US) 90292

(*) Notice: Subject to any disclaimer, the term of this patent is extended or adjusted under 35 U.S.C. 154(b) by 0 days.

(21) Appl. No.: 09/641,376

(22) Filed: Aug. 18, 2000

Related U.S. Application Data

(60) Provisional application No. 60/150,034, filed on Aug. 20, 1999.

(51) Int. Cl.$^7$ .............................................. A61K 35/78
(52) U.S. Cl. ........................ 424/725; 424/728; 424/752; 514/860
(58) Field of Search ................................ 424/725, 752, 424/728; 514/860

(56) References Cited

U.S. PATENT DOCUMENTS

| | | |
|---|---|---|
| 3,232,836 A | 2/1966 | Carlozzi et al. |
| 3,697,652 A | 10/1972 | Rovati et al. |
| 3,773,930 A | 11/1973 | Mohammed et al. |
| 4,285,964 A | 8/1981 | Niebes et al. |
| 4,414,202 A | 11/1983 | Silvetti |
| 4,424,232 A | 1/1984 | Parkinson |
| 4,486,416 A | 12/1984 | Soll et al. |
| 4,518,614 A | 5/1985 | Parkinson |
| 4,642,340 A | 2/1987 | Senin et al. |
| 4,647,453 A | 3/1987 | Meisner |
| 4,716,224 A | 12/1987 | Sakurai et al. |
| 4,938,969 A | 7/1990 | Schinitisky et al. |
| 4,956,173 A | 9/1990 | Le Fur et al. |
| 5,153,174 A | 10/1992 | Band et al. |
| 5,162,303 A | 11/1992 | Goodman |
| 5,198,465 A | 3/1993 | Dioguardi |
| 5,281,196 A | 1/1994 | Sultenfuss |
| 5,296,500 A | 3/1994 | Hillebrand |
| 5,308,627 A | 5/1994 | Umbdenstock, Jr. |
| 5,332,579 A | 7/1994 | Umbdenstock |
| 5,364,845 A | 11/1994 | Henderson |
| 5,371,089 A | 12/1994 | Rattan |
| 5,415,875 A | 5/1995 | Kakoki et al. |
| 5,529,769 A | 6/1996 | Cho et al. |
| 5,587,363 A | 12/1996 | Henderson |
| 5,730,988 A | * 3/1998 | Womack |
| 5,962,482 A | 10/1999 | Bissett |
| 6,093,411 A | 7/2000 | Bissett |
| 6,147,054 A | * 11/2000 | DePaoli Ambrosi |
| 6,156,347 A | * 12/2000 | Blatt et al. |

FOREIGN PATENT DOCUMENTS

| | | |
|---|---|---|
| CA | 1181693 | 1/1985 |
| CA | 2066306 | 10/1992 |
| EP | 0 167 363 A2 | 1/1986 |
| EP | 306377 A1 * | 3/1989 |
| GB | 896940 | 5/1962 |
| JP | 4029915 A | 2/1992 |

OTHER PUBLICATIONS

Lubell, A., "Antioxidants, Aging and the Skin", *Cosmetic Dermatology*, 9(7):58–60(1996).

Medline Abs., Swain, R., et al., "Vitamins As Therapy in the 1990's", *J. American Board of Family Practice*, 8(3):206–16 (1995).

Medline Abs., Todd, S., et al., "An investigation of the relationship between antioxidant vitamin intake and coronary heart disease in men and women using logistic regression analysis", *J. Clinical Epidemiology*, 48(2):307–16 (1995).

Medline Abs., Nachbar, F., et al., "The role of Vitamine E in normal and damaged skin", *J. Molecular Medicine*, 73(1):7–17 (1995).

Medline Abs., Werman, M.J., et al., "Gender, dietary cooper and carbohydrate source influence cardiac collegen and lysyl oxidase in weanling rats", *J. Nutrition*, 125(4):857–63 (1995).

Medline Abs., Shan, Z., et al., "Intracellular glutathione influences collagen generation by mesangial cells", *Kidney International*, 46(2):388–95 (1994).

Medline Abs., Maffei, F., et al., "Free radicals scavanging action and anti–enzyme activities of procyandines from *Vitis vinifera*. A mechansim for their capillary action", *Arzneimittal–Forschung*, 44(5):592–601 (1994).

Medline Abs., Oyama, Y., et al., "Myricetin and quercetin, the flavonoid constituents of Ginko Biloba extract greatly reduce oxidative metabolism in both resting and Ca(2+)–loaded brain neurons", *Brain Research*, 635(1–2):125–9 (1994).

(List continued on next page.)

*Primary Examiner*—Christopher R. Tate
*Assistant Examiner*—Michele C. Flood
(74) *Attorney, Agent, or Firm*—Pennie & Edmonds LLP

(57) ABSTRACT

Compositions and methods for reducing or eliminating the appearance of cellulite. The method involves administering to a patient in need of treatment therapeutically effective amounts of a sugar compound that is converted to a glycosaminoglycan in the patient in an amount sufficient to thicken the skin, a primary antioxidant component in an amount sufficient to substantially inhibit the formation of collagenase and elastase, at least one amino acid component in an amount sufficient to assist in the thickening of the skin, and at least one transition metal component in an amount effective to bind collagen and elastic fibers and thicken skin so as to reduce or eliminate the appearance of cellulite. A preferred method of treatment further includes administering the components above in conjunction with a vascular dilator to improve blood supply to the skin and/or a fat burner to reduce absorption or digestion of fat in the digestive tract or to prevent the production of fat. The compositions and methods may optionally include chromium picolinate to facilitate entry of sugar into cells to improve fat metabolism. In one embodiment, these methods encompass administering the amounts as a pharmaceutical composition.

16 Claims, No Drawings

OTHER PUBLICATIONS

Medline Abs., Asman, B., et al., "Reduction of collagen degredation in experimental granulation tissue by vitamin E and selenium", *J. Clinical Periodontology*, 21(1):45–7 (1994).

Nelder, K.H., "Nutrition and the Skin", Amer. Acad. Derm. Annl. Mtg., Dec. 6, 1993.

Medline Abs., Xie, B., et al., "Antioxident properties of fractions and polyphenol constituents from green, oolong and black teas", *Life Sciences*, 17(2):77–84 (1993).

Medline Abs., Parto, K. et al., "Osteoporosis in lysinuric protein intolerance", *J. Inherited Metabolic Disease* 16(2):441–50 (1993).

Medline Abs., Gimenez, A., et al., "Influence on dietary zinc on hepatic collagen and prolyl hydroxlase activities in alcoholic rats", *Hepatology*, 16(3):815–9 (1992).

Medline Abs., Reiser, K., et al., "Enzymatic and nonenzymatic cross–linking of collagen and elastin", *Faseb Journal*, 6(7):2439–49 (1992).

Bucci, L., et al., Glucosamine—A New Potent Nutraceutical for Connective Tissues, *Nutritional Supplement Advisor*, Jul. 1992.

Medline Abs., Deucher, G.P., "Antioxidant therapy in the aging process", 62:428–37 (1992).

Medline Abs., Pihlajaniemi, T., et al., "Prolyl 4–hydroxylase and its roles in collagen synthesis", *J. Hepatology*, 12 Supp(3):S2–7 (1991).

Thomas, P., "Vitamin C Eyed for Topical Use as Skin Preserver", *Medical World News*, Mar., 1991, p. 12.

Grevenstein, J., et al., "Cartilage Changes in Rats Induced by Papain and the Influence of Treatment With N–Acetylglucosamine", *Acta Orthopaedica Belgica*, 57(2):157–161 (1991).

Cerimele, D., et al., "Physiological Changes in Ageing Skin", *British Journal of Dermatology* (1990) I11, Supplement 35, pp. 13–20.

Medline Abs., Zafirov, D., et al., "Antiexudative and capillaritonic effects of procyanidines isolated from grape seeds (*V. Vinifera*)", *Acta Physiologica et Pharmacologica Bulgarica*, 16(3):50–4 (1990).

Medline Abs., Stoss, H., "Pathologic anatomy of osteogenesis imperfecta. Light and electron microsopic studies of supportive tissue and skin", *Veroffentlichungen aus der Pathologie*, 134:1–88 (1990).

Reddy, G.K., et. al., "Studies on the Metabolism of Glycosaminoglycans Under the Influence of New Herbal Anti–Inflammatory Agents", *Biochemical Pharmacology*, 38(20):3527–3534 (1989).

Fenske, N., et al., "Structural and Functional Changes of Normal Aging Skin", *Journal of the American Academy of Dermatology*, 15(4):571–585, Part 1 (1986).

Setnikar, I., et al., "Pharmacokinetics of Glucosamine in the Dog and in Man", *Arneim. Forsch/Drug Res.* 36(1):729–733, No. 4 (1986).

Kuijer, R., et al., "Influence of Constituents of Proteoglycans on Type II Collagen Fibrillogenesis", *Collagen and Related Research*, 5:379–91 (1985).

Tapadinhas, M.J., et al., "Oral Glucosamine Sulphate in the Management of Arthrosis: Report on a Multi–Centre Open Investigation in Portugal", *Pharmatherapeutica*, 3(3):157–168 (1982).

D'Ambrosio, E., et al., "Glucosamine Sulphate: A Controlled Clinical Investigation in Arthrosis", *Pharmatherapeutica*, 2(8):504–508 (1981).

Drovanti, A., et al., "Therapeutic Activity of Oral Glucosamine Sulfate in Osteoarthrosis: A Placebo–Controlled Double–Blind Investigation", *Clinical Therapeutics*, 3(4):1–6 (1980).

Montagna, W., et al., "Structural Changes in Aging Human Skin", *The Journal of Investigative Dermatology*, 73(1):47–53 (1979).

Murray, M. T., "Arthritis—A Natural Solution".

* cited by examiner

PHARMACEUTICAL COMPOSITIONS FOR REDUCING THE APPEARANCE OF CELLULITE

This application claims benefit of Provisional Appln. No. 60/150,034 filed Aug. 20, 1999.

TECHNICAL FIELD

This application relates to methods to supplement collagen and elastic tissues and thicken the dermis to reduce or eliminate the appearance of cellulite.

BACKGROUND OF THE INVENTION

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by the structural changes in the skin due to aging and excessive sun exposure. The physiological changes associated with skin aging include impairment of the barrier function and decreased turnover of epidermal cells, for example. [Cerimele, D., et al., *Br. J. Dermatol.*, 122 Suppl. 35, p. 13–20 (April 1990)].

The mechanical properties of the skin, such as elasticity, are controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, bumps, braises or wrinkles, it roughens, and it has reduced ability to synthesize Vitamin D. Aged skin also becomes thinner and has a flattened dermoepidermal interface because of the alterations in collagen, elastin, and glycosaminoglycans. [Fenske, N. A, and Lober, C. W., *J. Am. Acad. Dermatol.*, 15:571–585 (Oct. 1986); Montagna, W. and Carlisle, K., *Journal of investigative Dermatol.*, 73(1):47–53 (1979)].

Cellulite is a cosmetic/medical condition caused by defects in the skin that result in the skin having an "orange peel" or "cottage cheese" effect. Cellulite is typically characterized by dermal deterioration due to a breakdown in blood vessel integrity and a loss of capillary networks in the dermal and subdermal levels of the skin. The vascular deterioration tends to decrease the dermal metabolism. This decreased metabolism hinders protein synthesis and repair processes, which results in dermal thinning. The condition is further characterized by fat cells becoming engorged with lipids, swelling, and clumping together, as well as excess fluid retention in the dermal and subdermal regions of the skin. Thus, individuals afflicted with cellulite tend to have a thicker subcutaneous fatty layer of skin. In the advanced stages of cellulite, reticular protein deposits called septa begin to form around the fatty deposits in the skin and occlude the fat cells. As the condition further progresses, hard nodules of fat cells and clumps of fat surrounded by septa form in the dermal region. This leads to the surface of the skin displaying considerable heterogeneity and being characterized as having a "cottage cheese" appearance. This appearance is most pronounced in overweight individuals. Individuals with cellulite also tend to have a thinner epidermis and dermis in the affected region, decreased firmness of the skin, and decreased rate of cell renewal.

The appearance of cellulite currently tends to be treated by administering xanthines, which include caffeine, theophylline, and aminophylline. Xanthines acts as a diuretic that removes water from the fat cells and thus reduces the size of the fat cells. The effect of xanthines, however, is temporary and the fat cells become rehydrated as soon as the individual replenishes the lost water.

A variety of vitamins and minerals have individually been administered to treat certain skin and other problems that occur when the patient has a deficiency of that vitamin or mineral. Vitamin A, for example, assists in the treatment of acne and to facilitate wound healing; vitamin C (ascorbic acid) assists in the prevention of skin bruising and wound healing; vitamin E is an antioxidant; and copper assists in the treatment of elastic tissue defects. [Neldner, K. H., *Amer. Acad. Derm. Ann. Mtg.*, Wash D.C., Dec. 6, 1993]. Topical use of vitamin C is also believed to ward off sun damage, reduce breakdown of connective tissues, and possibly promote collagen synthesis. [Dial, W., *Medical World News*, p. 12, March 1991]. Vitamin E is used topically as an anti-inflammatory agent, for enhancement of skin moisturization, for UV-ray protection of cells, and for retardation of premature skin aging.

Catechin-based preparations, including proanthanols and proanthocyanidins are powerful antioxidants. These compounds are found in flowers, plant leaves, and grape seeds, for example. [Lubell, A., *Cosmetic Dermatol.*, 9(7):58 & 60 (July 1996)].

N-Acetylglucosamine and glucosamine have been examined for use in the prevention and treatment of degenerative joint diseases and cartilage loss, and found to increase the glycosaminoglycans present in the cartilage to restore cartilage. [See Grevenstein, J., et al., *Acta Orthopaedia Belgica*, 57(2):157–161 (1991); Setnikar, I., *Drug Res.*, 36(4):720–733 (1986); Drovanti, A., et al, *Clin. Therap.*, 3(4):1–6 (1980)]. Glucosamine has also been examined in connection with arthritis [See, e.g., Murray, M. T.] and oral and injected glucosamine have been reported to be useful for arthrosic patients. [Tapadinhas, M. J., et al., *Pharmatherapeutica*, 3(3):157–168 (1982); D'Ambrosio, E., et al., *Pharmatherapeutica*, 2(8):504–508 (1981)].

The metabolism of glycosaminoglycans under the influence of herbal and other anti-inflammatory agents has been examined by measuring glycosaminoglycans in the skin, liver, kidney, and spleen after administration of several compounds. [Reddy, G. K., et al., *Biochem. Pharmacology*, 38(20):3527–3534 (1989)].

In addition to their individual use to supplement a deficiency in a patient, various of the above ingredients have been combined to form pharmaceuticals designed to prevent and treat certain cellular, skin, and other conditions. For example, U.S. Pat. No. 3,773,930 discloses a low residue, dietary composition having at least one amino acid and a quantity of non-amino acid derived caloric material sufficient to obviate the diarrhea problem of straight amino acid compositions. A flavoring material may also be included to render the composition more palatable.

U.S. Pat. No. 4,285,964 discloses a salt of (+)-catechin formed by reacting (+)-catechin with at least a basic amino acid, such as L-lysine and L-arginine; and a hydrosoluble double salt formed from the reaction product of (+)-catechin with a basic amino-acid, such as L-lysine and L-arginine, and another inorganic or organic acid. The patent further discloses methods of treating degenerative diseases of the connective tissue by topically administering the composition.

U.S. Pat. No. 4,414,202 discloses a composition for the treatment of skin wounds with a buffered salt solution having a pH between 6 to 7.8 and administering a starch hydrolysate compound, and preferably including alphaketoglutaric acid or alphaketoglutarate salts. Optional additives to the composition include ascorbic acid or salts thereof, ferrous salts, and glycine, L-Proline, and L-Lysine.

U.S. Pat. No. 4,424,232 discloses a topical composition for the treatment of herpes simplex, cold sores, lesions, and other painful skin conditions including L-lysine, gibberellic acid, and urea in an inert carrier having water. The composition may also include L-ascorbic acid, as well as methyl paraben, propyl paraben, or mixtures thereof.

U.S. Pat. No. 4,647,453 discloses a method and composition for treatment of tissue degenerative inflammatory disease in animals and humans by oral administration of ascorbic acid, bioavailable calcium, a precursor or stimulant of epinephrine or nor-epinephrine of tyrosine or phenylalanine, and an anti-inflammatory substance selected from anti-inflammatory sugars, amino sugars and biocompatible acid addition salts thereof, and anti-inflammatory amino acids, to promote connective tissue regrowth.

U.S. Pat. No. 5,198,465 discloses a composition for treating precursor deficiencies in the synthesis of collagen with proline, glycine, lysine, vitamin C, and one or more compounds selected from α-ketoglutaric acid, methionine, cysteine, cystine, valine, and pharmaceutically acceptable diluents and excipients.

U.S. Pat. Nos. 5,332,579 and 5,308,627 disclose a nutritional supplement to assist persons recovering from addiction by administering a variety of vitamins and minerals including enzyme activating substances such as magnesium and zinc; an enzyme co-factor that is a vitamin like various vitamin B complexes; an enzyme producer such as an amino acid like glutamic acid; an herbal antispasmodic substance like Valerian root; and vitamin C.

U.S. Pat. No. 5,415,875 discloses a method of suppressing formation of lipid peroxide and removing peroxide by applying to the skin a decomposed product of shell membrane and tocopherol and derivatives. Lysine, proline, Vitamin C, for examples, are listed among a vast genus of optional additives.

The above references, however, do not teach pharmaceutical compositions or methods for reducing or eliminating the appearance of cellulite. The present invention provides such a method. The method reduces or eliminates the appearance of cellulite by administering to a patient in need of treatment a composition that supplements collagen and elastic tissue in the skin and thickens the dermis.

SUMMARY OF THE INVENTION

The present invention relates to compositions for reducing or eliminating the appearance of cellulite in a patient. The composition includes a sugar compound that is converted to a glycosaminoglycan in the patient in an amount sufficient to thicken the skin, a primary antioxidant component in an amount sufficient to substantially inhibit the activity of collagenase and elastase, at least one amino acid component in an amount sufficient to assist in the thickening of the skin, and at least one transition metal component in an amount effective to bind collagen and elastic fibers and thicken the skin. In a preferred embodiment, the composition further includes at least one fat burner to reduce absorption of fat in the digestive tract or prevent the production of fat. In another preferred embodiment, the composition further includes at least one vascular dilator to improve blood supply to the skin.

The invention further relates to methods for reducing or eliminating the appearance of cellulite. The method involves administering to a patient in need of treatment a sugar compound that is converted to a glycosaminoglycan in the patient in an amount sufficient to thicken the skin, a primary antioxidant component in an amount sufficient to substantially inhibit the activity of collagenase and elastase in the skin, at least one amino acid component in an amount sufficient to assist in the thickening of the skin, and at least one transition metal component in an amount effective to bind collagen and elastic fibers and thicken skin, so as to modify the thickness of the skin to reduce or eliminate the appearance of cellulite.

The sugar, the primary antioxidant, at least one amino acid component, and at least one transition metal component may be administered sequentially, as well as simultaneously in the form of a single pharmaceutical composition, or in any combination thereof. The composition may be administered orally or topically. When the composition is administered orally it may be administered as a tablet or capsule having 1 mg to 2,000 mg of the composition. When the composition is administered topically it is preferably administered with one or more mono- or poly-hydroxy acids, a mixture thereof, or a pharmaceutically acceptable salt or ester thereof in an amount sufficient to exfoliate at least a portion of the skin. The mono- or poly-hydroxy acid may be tannic acid or salicylic acid.

In a preferred embodiment, the method further includes administering at least one fat burner in an amount sufficient to reduce absorption of fat in the digestive tract or prevent the production of fat. The sugar, the primary antioxidant, the at least one amino acid component, the at least one transition metal component, and the at least one fat burner may be administered sequentially, simultaneously as a pharmaceutical composition, or in any combination thereof, e.g., a composition of the first four components followed by the at least one fat burner.

In another preferred embodiment, the method further includes administering at least one vascular dilator in an amount sufficient to improve blood supply to the skin. The sugar, the primary antioxidant, the at least one amino acid component, the at least one transition metal component, and the at least one vascular dilator may be administered sequentially, simultaneously as a pharmaceutical composition, or in any combination thereof.

In another embodiment, the sugar, the primary antioxidant, the at least one amino acid component, the at least one transition metal component, and the at least one vascular dilator may be administered in conjunction with at least one fat burner to reduce absorption of fat in the digestive tract or prevent the production of fat.

Preferred fat burners include hydroxy citric acid, chitin, or a mixture thereof. When the fat burner is hydroxy citric acid, it is preferable to administer about 750 mg to 1500 mg of hydroxy citric acid. When the fat burner is chitin, it is preferable to administer from about 1000 mg to 2000 mg of chitin.

Preferred vascular dilators include extract of ginko biloba, ginsing, phenylalanine, or a mixture thereof. When the vascular dilator is extract of ginko biloba, it is preferable to administer from about 5 mg to 300 mg of extract of ginko biloba. When the vascular dilator is ginsing it is preferable to administer from about 100 mg to 200 mg of ginsing extract When the vascular dilator is phenylalanine it is preferable to administer from about 75 mg to 1500 mg of phenylalanine. A sufficient amount of vascular dilator can readily be determined by one of ordinary skill in the art.

Optionally the sugar, the primary antioxidant, the at least one amino acid component, the at least one transition metal component, and/or vascular dilator, and/or fat burner can be administered with from about 10 mg to 500 mg of chromium picolinate to facilitate entry of sugar into cells to improve metabolism of fats by the body.

DETAILED DESCRIPTION OF THE PREFERRED EMBODIMENTS

A method for reducing or eliminating the appearance of cellulite has now been discovered. The method includes administering to a human in need of treatment therapeutically sufficient amounts of at least one sugar compound which is converted into glycosaminoglycans in the bloodstream, a primary antioxidant component, at least one amino acid component, and at least one transition metal component, so as to modify the thickness of the skin to reduce or eliminate the appearance of cellulite. Without wishing to be bound by theory, Applicant believes that a thicker dermis desirably reduces the appearance of cellulite that occurs when areas of the skin become thin. Improved compositions have also been discovered that are used in preferred methods. These compositions and methods preferably include a vascular dilator and/or a fat burner. Furthermore, the compositions and methods of the present invention result in stronger blood vessels. Skin and blood vessels are both connective tissues and thus, without wishing to be bound by theory, it is believed that the blood vessels are strengthened by the same process that leads to thickening of the skin.

The composition preferably contains at least one sugar compound, and more preferably just one sugar compound, present in about 5 to 50 weight percent, preferably about 10 to 40 weight percent, and more preferably about 15 to 30 weight percent of the composition. The primary antioxidant component is preferably present in an amount of about 5 to 50 weight percent, more preferably about 10 to 40 weight percent, and most preferably about 15 to 30 weight percent of the composition. The amino acid component is preferably present in about 8 to 60 weight percent, more preferably about 15 to 50 weight percent, most preferably about 20 to 40 weight percent of the composition. The transition metal component is preferably present in about 0.5 to 15 weight percent, more preferably present in about 2 to 12 weight percent, and most preferably present in about 5 to 10 weight percent of the composition.

The first component of the composition is any sugar compound that is converted to a glycosaminoglycan in the human bloodstream. Typically, this would be an N-acetylglucosamine compound, or a pharmaceutically acceptable salt or ester thereof. The N-acetylglucosamine component may be N-acetylglucosamine or any pharmaceutically acceptable salt or ester thereof, but more preferably is the N-acetylglucosamine only. This component must be present in sufficient quantity in the pharmaceutical composition to promote thickening of the dermis. Without wishing to be bound by theory it is believed that one mechanism by which glycosaminoglycans help thicken the skin is by improving the skins ability to absorb moisture. It is also believed that glycosaminoglycans are an important factor in assisting fibroblasts in producing collagen and elastic tissue. Thus, it can be advantageous to administer the composition in conjunction with a topically administered exfoliant that further improves the skin's ability to absorb moisture by removing dead and dying skin cells from at least a portion of the skin. The N-acetylglucosamine is present in about 5 to 30 weight percent, preferably 8 to 27 weight percent, and more preferably 12 to 24 weight percent of the pharmaceutical composition. A unit dose of N-acetylglucosamine is typically about 40 mg to 250 mg, preferably about 60 to 200, and more preferably about 100 mg to 200 mg.

The pharmaceutical composition includes a primary antioxidant component, which typically includes a vitamin C source and preferably is ascorbic acid, or a pharmaceutically acceptable salt or ester thereof, and more preferably is ascorbyl palmitate, dipalmitate L-ascorbate, sodium L-ascorbate-2-sulfate, glucosamine ascorbate, or an ascorbic salt, such as sodium, potassium, or calcium ascorbate, or mixtures thereof. The antioxidant component inhibits collagenase and elastase, enzymes that break down collagen and elastic tissues. In addition, vitamin C also strengthens blood vessels. When oral formulations of the pharmaceutical composition are used, it is preferred that a non-acidic form of vitamin C be used to reduce the stomach irritation that may occur when using an acidic form. The vitamin C source is present in the pharmaceutical composition in about 5 to 50 weight percent, preferably about 7 to 40 weight percent, and more preferably about 10 to 25 weight percent. A unit dose when a vitamin C source is the primary antioxidant component is typically from about 40 mg to 400 mg, preferably about 60 mg to 300 mg, and more preferably about 80 mg to 150 mg. Vitamin C is also approved by the FDA and has wide consumer acceptance, so that it can be used in amounts as high as 10,000 mg, if desired.

The pharmaceutical composition also includes at least one amino acid to assist in thickening the skin. The amino acids assist in the thickening of the dermis, supplementing of collagen and elastic tissues and, consequently, reducing or eliminating the appearance of cellulite. Preferably two or more amino acids are used in combination. Either the L- or D- forms of amino acids are acceptable. Lysine or proline are the most preferred amino acids and they are advantageously used in combination. Cysteine, glycine, methionine or other amino acids can also be used, if desired. The amino acid(s) may be included in a soluble form such as the hydrochloride, i.e., L-Lysine hydrochloride. The amino acid (s) are present in an amount of about 2 to 25 weight percent each, preferably about 4 to 20 weight percent each, and more preferably about 6 to 15 weight percent each. A unit dose for each amino acid is typically about 35 mg to 200 mg each, preferably about 50 mg to 150 mg each, and more preferably about 70 mg to 120 mg in the pharmaceutical composition. Additional useful forms of amino acid include the following: a cysteine source, preferably N-acetyl cysteine, can be present in an amount of about 1 to 10 weight percent, preferably about 2 to 8 weight percent, and more preferably about 3 to 6 weight percent of the pharmaceutical composition. A methionine source, preferably L-selenomethionine, can be present in an amount of about 0.1 to 5 weight percent, preferably 0.2 to 3 weight percent, and more preferably 0.3 to 1 weight percent of the composition, wherein the selenium component is from about 0.1 to 3 weight percent of the methionine source.

One or more transition metal compounds are included in an amount effective to bind collagen and elastic tissue to rebuild the skin. Certain transition metal compounds also inhibit elastase, an enzyme that also breaks down collagen and elastic tissue. Preferred transition metals include zinc, manganese and copper, with combinations thereof being most preferred.

A zinc component can be included to assist in binding collagen and elastic fibers, which both assists in the rebuilding of skin. The zinc component may be any zinc compound or pharmaceutically acceptable salt thereof, but more preferably is a zinc complexed with an amino acid, and most preferably is zinc monomethionine, wherein the zinc is typically present in about 10 to 30 weight percent of the complex. The zinc component is present in about 1 to 10 weight percent, more preferably about 2 to 7 weight percent, and most preferably about 3 to 5 weight percent of the pharmaceutical composition.

A manganese component can also be included to assist in binding collagen and elastic fibers. The manganese component may be any manganese compound or pharmaceutically acceptable salt thereof, but more preferably is a manganese component which is at least partially complexed with a vitamin C source, and most preferably is manganese ascorbate or manganese ascorbic acid, wherein the manganese is typically present in about 5 to 20 weight percent of the complex. When complexed with vitamin C, this vitamin C source may be included in the overall percentage of vitamin C in the pharmaceutical composition. The manganese component is typically present in about 1 to 10 weight percent, more preferably about 2 to 7 weight percent, and most preferably about 2.5 to 4 weight percent of the pharmaceutical composition.

A copper component is preferably also included in the pharmaceutical composition, and may be any copper compound or pharmaceutically acceptable salt thereof, but preferably is copper sebacate, wherein the copper is typically present in about 5 to 20 weight percent of the copper sebacate. The copper component also inhibits elastase and is present in about 0.1 to 5 weight percent, preferably about 0.2 to 3 weight percent, and more preferably about 0.3 to 1 weight percent of the pharmaceutical composition. A unit dose of the copper component of the pharmaceutical composition may include about 1 mg to 40 mg, preferably about 2 mg to 25 mg, and more preferably about 2.5 mg to 10 mg of.

In another preferred form of the invention, the pharmaceutical composition further includes a catechin-based preparation, such as a proanthanol or proanthocyanidin, along with glucosamine or a pharmaceutically acceptable salt or ester thereof, and chondroitin or a pharmaceutically acceptable salt or ester thereof.

The catechin-based preparation, similar to vitamin C, inhibits elastase and collagenase, which is another enzyme that attacks elastic tissue and collagen. The catechin-based preparation is preferably a proanthanol or proanthocyanidin, more preferably a proanthocyanidin, and most preferably grape seed extract. These compounds are considered to be secondary antioxidants, because they are present in lesser amounts than the primary antioxidant. The catechin-based preparation is present in about 0.5 to 5 weight percent, more preferably about 0.6 to 3 weight percent, and most preferably about 0.7 to 2 weight percent of the pharmaceutical composition.

The glucosamine or a pharmaceutically acceptable salt or ester thereof, and the chondroitin or a pharmaceutically acceptable salt or ester thereof, are each present in about 3 to 17 weight percent, preferably about 4 to 12 weight percent each, and more preferably about 5 to 8 weight percent each of the pharmaceutical composition. The glucosamine component preferably is present as a sulfate or succinate, and more preferably is D-glucosamine sulfate, wherein the glucosamine is preferably present as about 60 to 90 weight percent of the salt. The glucosamine content of this component contributes to the formation of glycosoaminoglycans in the skin. The chondroitin component preferably is present as a sulfate or succinate, and more preferably is chondroitin sulfate, wherein the chondroitin is preferably present as about 65 to 95 weight percent of the salt.

In another preferred embodiment, the pharmaceutical composition includes at least one fruit extract, which provides antioxidants that are naturally present in the fruit extracts. Preferably, the fruit extract is obtained from apricots, apples, pears, peaches, pineapples, papayas, cherries, kiwis, tangerines, or oranges. Most preferably, the fruit extract is obtained from pomegranate. The fruit extract is preferably present in an amount of about 0.01 to 80 weight percent and more preferably in about 0.1 to 20 weight percent of the pharmaceutical composition. A preferred oral daily dose range of the fruit extract, when included in the composition, should be from about 0.01 mg to 2,000 mg; more preferably about 400 mg to 1,600 mg; and most preferably about 800 mg to 1,200 mg. In general, a preferred topical daily dosage range, in single or divided doses, should be from about 0.01 mg to 20,000 mg, more preferably about 2,000 mg to 16,000 mg and most preferably 6,000 mg to 10,000 mg of the fruit extract.

In a more preferred form, several optional additives are included in the pharmaceutical composition, such as a vitamin E source, a vitamin $B_3$ source, quercetin powder, pyridoxal 5 phosphate-Co $B_6$, and a vitamin A source. The vitamin E preferably is a sulfate or succinate vitamin E complex, and more preferably is D-alpha tocopheryl acid succinate. The vitamin E source is present in about 1 to 15 weight percent, preferably about 2 to 12 weight percent, and more preferably about 3 to 10 weight percent of the composition. In any event, no more than 1,500 IU should be ingested per day, as Vitamin E becomes toxic at higher doses. The vitamin $B_3$ source preferably is niacinamide, and the source is present in about 0.5 to 15 weight percent, preferably about 1 to 12 weight percent, and more preferably about 1.5 to 10 weight percent of the composition. The vitamin A source preferably is vitamin A palmitate, and the source is present in about 0.1 to 5 weight percent, preferably 0.2 to 3 weight percent, and more preferably 0.3 to 1 weight percent of the composition. Vitamin A is toxic at high levels, such that no more than 400,000 IU should be cumulatively ingested per day for greater than six months. The quercetin powder is quercetin dihydrate, which is typically present in about 0.5 to 15 weight percent, preferably about 1 to 12 weight percent, and more preferably about 1.5 to 10 weight percent of the composition. The pyridoxal 5 phosphate-Co $B_6$, also known as P-5-P monohydrate, is typically present in about 0.1 to 5 weight percent, preferably 0.2 to 3 weight percent, and more preferably 0.3 to 1 weight percent of the composition.

In another preferred form, the pharmaceutical composition also includes at least one vascular dilator or "fat burner."

The vascular dilator may be administered in an amount sufficient to improve blood supply to the skin. Without wishing to be bound by theory, vascular dilators are also believed to strengthen blood vessels. Any suitable compound that improves blood supply to the skin available to one of ordinary skill in the art may be used. Vascular dilators include, but are not limited to, ginko biloba, ginsing, phenylalanine, and mixtures thereof. When the vascular dilator is ginsing it is preferable to administer from about 100 mg to 200 mg per day of a standardized herbal extract of ginsing that supplies approximately 4–7% ginsenosides, the active ingredients in ginsing. When the vascular dilator is phenylalanine it is preferable to administer from about 75 mg to 1500 mg of phenylalanine per day. The typical dose for phenylalanine is 200 mg administered three times per day. The preferred vascular dilator is extract of ginko biloba. Extract of ginko biloba contains as the active ingredient the vascular dilator ginkoflavone glycoside. A unit dose of ginko biloba is typically about 5 mg to 300 mg, preferably about 20 mg to 200 mg, and more preferably about 40 mg to 160 mg. The most preferred form of the vascular dilator is two tablets per day each containing about 60 mg of ginko biloba extract. A sufficient amount of vascular dilator can readily be determined by one of ordinary skill in the art.

"Fat burners" are compounds that reduce absorption of fat in the digestive tract, preferably also the digestion of fat and prevents or inhibits the production of fat. Any suitable compound that reduces absorption, or digestion of fat in the digestive tract, or prevents or inhibits the production of fat may be used. Preferred "fat burners" include hydroxy citric acid and chitin. Hydroxy citric acid is believed to prevent or inhibit carbohydrates from being converted into fat. A unit dose of hydroxy citric acid is up to about 3000 mg, preferably from about 500 mg to 2500 mg, more preferably from about 750 mg to 1500 mg. The preferred source of hydroxy citric acid is extract of *garcinia cambogia*. Thus, when a "fat burner" is included in the compositions or methods of the invention, it is preferred to administer about 1500 mg to 3000 mg of extract of *garcinia cambogia*, which typically contains about 50 percent hydroxy citric acid. Chitin interferes with the absorption of fat in the intestinal tract by binding with fat molecules to form large masses that the body cannot absorb and are excreted. Chitin can be administered in any amount, but it is typically administered in an amount from about 1000 mg to 2000 mg. A sufficient amount of fat burner can readily be determined by one of ordinary skill in the art.

Optionally, the composition further includes chromium picolinate. Chromium picolinate facilitates entry of sugar into cells and thus enhances the body's ability to utilize nutrients and its own energy resources. The more efficient utilization of energy resources includes more efficient metabolism of fats by the body. A typical unit dose for chromium picolinate, when included, is from about 10 mg to 500 mg, preferably from about 100 mg to 350 mg, and more preferably from about 150 mg to 250 mg.

Compositions and methods of the invention intended for topical application may optionally include an acidic component including one or more mono- or poly-hydroxy acids, a mixture thereof, or a pharmaceutically acceptable salt or ester thereof. One of ordinary skill in the art will be readily able to select and prepare suitable mono- or poly-hydroxy acids for use in the compositions and methods of the invention, for example, alkyl hydroxycarboxylic acids, aralkyl and aryl hydroxycarboxylic acids, polyhydroxy-carboxylic acids, and hydroxy-polycarboxylic acids. Exemplary mono- or poly-hydroxy acids include: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid; isocitric acid; agaricic acid; quinic acid; glucoronic acid; glucoronolactone; galactoronic acid; galactoronolactone; uronic acids; uronolactones; ascorbic acid; dihydroascorbic acid; dihydroxytartaric acid; tropic acid; ribonolactone; gluconolactone; galactonolactone; gulonolactone; mannonolactone; citramalic acid; pyruvic acid; hydroxypyruvic acid; hydroxypyruvic acid phosphate and esters thereof; methyl pyruvate; ethyl pyruvate; propyl pyruvate; isopropyl pyruvate; phenyl pyruvic acid and esters thereof; methyl phenyl pyruvate, ethyl phenyl pyruvate, and propyl phenyl pyruvate; formyl formic acid and esters thereof; methyl formyl formate, ethyl fornyl formate, and propyl formyl formate; benzoyl formic acid and esters thereof; methyl benzoyl formate, ethyl benzoyl formate, and propyl benzoyl formate; 4-hydroxybenzoyl formic acid and esters thereof; 4-hydroxyphenyl pyruvic acid and esters thereof; 2-hydroxyphenyl pyruvic acid and esters thereof; and mixtures thereof. The hydroxy acids are preferably selected from one or more alpha-hydroxy acids or beta-hydroxy acids, more preferably from glycolic, lactic, citric, tannic, or salicylic acid, and most preferably from citric or salicylic acids. It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370, which are incorporated herein by express reference thereto, are also suitable for use in the compositions and methods of the invention. The acidic component is administered topically in conjunction with the compositions and methods in an amount sufficient to exfoliate, i.e., remove dead or dying skin cells, from at least a portion of the skin. The acidic component, when used, is typically present in an amount from about 0.1 to 12 weight percent, preferably from about 1 to 11 weight percent, more preferably from about 4 to 10 weight percent of the composition. For example, the acidic component may be from about 0.1 to 3 weight percent citric acid in combination with up to about 2 weight percent salicylic acid.

The phrase "therapeutically effective amount" means that amount of active ingredient(s), e.g., in a pharmaceutical composition, that provides a therapeutic benefit in the reduction or elimination of the appearance of cellulite or in the treatment, prevention, or management of one or more skin conditions.

The magnitude of a prophylactic or therapeutic dose of the composition in the management of cellulite will vary with the severity of the condition to be treated and the route of adrninistration. The dose, and perhaps the dose frequency, will also vary according to the age, body weight, and response of the individual patient. In general, the total daily dose range, for the conditions described herein, is from about 10 mg to about 20,000 mg administered in single or divided doses orally, topically, transdermally, or locally by inhalation. For example, a typical oral daily dose range should be from about 10 mg to 20,000 mg, preferably about 2,000 mg to 16,000 mg, and more preferably about 6,000 mg to 10,000 mg of the active components (i.e., excluding excipients and carriers).

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The term "unit dose" is meant to describe a single dose, although a unit dose may be divided, if desired. About 1 to 10 unit doses of the present invention are typically administered per day, preferably about 2 to 6 doses per day, and more preferably about 4 doses per day.

Although any suitable route of administration may be employed for providing the patient with an effective dosage of the composition according to the methods of the present invention, preferred routes include, for example, oral, rectal, parenteral, intravenous, topical, transdermal, subcutaneous, intramuscular, and like forms of administration may be employed. More preferred routes include oral or topical administration. Suitable dosage forms include tablets, troches, dispersions, suspensions, solutions, capsules, patches, suppositories, and the like, although oral and topical dosage forms are preferred.

The pharmaceutical compositions used in the methods of the present invention include the active ingredients described above, and may also contain pharmaceutically acceptable carriers, excipients and the like, and optionally, other therapeutic ingredients. The active ingredients used in the methods and compositions can be administered individually, as a single composition that contains all the ingredients, or in any combination thereof.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, faroic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (Nmethylglucamine), and procaine.

The compositions for use in the methods of the present invention may be prepared in various formulations, such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

Pharmaceutical compositions for use in the methods of the present invention may be presented as discrete units such as capsules, cachets, tablets, or aerosol sprays, each containing a predetermined amount of the active ingredient, as a powder, stick, or granules, as creams (e.g., a conditioner), pastes, gels, lotions, syrups, ointments, sponges or cotton applicators, or as a solution or a suspension in an aqueous liquid, a non-aqueous liquid, an oil-in-water emulsion, or a water-in-oil liquid emulsion.

Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each unit dose, i.e., tablet, cachet or capsule, contains from about 1 mg to 2,000 mg of the active ingredient, preferably about 200 mg to 1,600 mg, and more preferably about 600 mg to 1,000 mg of the composition.

The compounds for use in the methods of the present invention may also be administered topically. Topical administration advantageously helps thicken the epidermis. Because of its ease of administration, a cream, lotion, or ointment represents the most advantageous topical dosage form, in which case liquid pharmaceutical carriers may be employed in the composition. These creams, lotions, or ointments, may be prepared as rinse-off or leave-on products. Each of these forms is well understood by those of ordinary skill in the art, such that dosages may be easily prepared to incorporate the pharmaceutical composition of the invention.

In addition to the common dosage forms set out above, the compounds of the invention can also be administered by controlled-release means or delivery devices that are well known to those of ordinary skill in the art, such as those described in U.S. Patent Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are incorporated herein by reference. Preferred controlled-release means are disclosed by: U.S. Pat. Nos. 5,427,798 and 5,486,362; WO 9404138; CA 1239034; and European Patent Application Nos. 467488 and 171457, all of which are incorporated herein by reference. These dosage forms can be used to provide slow or controlled-release of one or more of the active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1

Capsules

A large number of unit capsules were prepared by filling standard two-piece hard gelatin capsules each with the desired amount of powdered active ingredient as described above, 150 milligrams of lactose, 50 milligrams of cellulose, and 6 milligrams magnesium stearate.

Example 2

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing the desired amount of the active ingredient. The capsules are washed and dried for packaging.

Example 3

Tablets

A large number of tablets were prepared by conventional procedures so that the dosage unit included: the desired amount of active ingredient as described herein, 50 milligrams of red beet root powder, 12 milligrams of stearic acid, 10.95 milligrams of sorbitol, 3 milligrams of acdisol, 1 milligram of magnesium stearate, and 1 milligram of syloid. Appropriate coatings may be applied to increase palatability or delay absorption. A specific therapeutic formulation of the pharmaceutical composition prepared in accordance with the invention is set forth in the table below:

| Ingredient | Weight Percent (% w/w) | Amount (mg) | Chemical or Scientific Name (if different) |
|---|---|---|---|
| N-Acetylglucosamine | 17.1 | 140 | N-Acetyl D-Glucosamine |
| Vitamin C (81.2% Ascorbic Acid) | 15 | 123.2 | |
| L-Lysine (80%) | 12.2 | 100 | L-Lysine hydrochloride |
| L-Proline | 11 | 90 | |
| D-Glucosamine Sulfate (75%) | 6.5 | 53.3 | |
| Chondroitin Sulfate (80%) | 6.1 | 50 | |
| Vitamin E Succinate | 4.3 | 39.7 | D-α tocopheryl acid succinate |
| Zinc monomethionine (20%) | 3.7 | 30 | Zinc DL-methionine |
| N-Acetyl Cysteine | 3.7 | 30 | |
| Manganese Ascorbate (13% Mn) | 2.8 | 23.1 | |
| Vitamin $B_3$ Niacinamide | 2.4 | 20 | Niacinamide |
| Quercetin Powder | 2.4 | 20 | Quercetin dihydrate |
| Grape Seed Extract | 0.9 | 7.5 | Proanthocyanidin |
| Pyridoxal 5 Phosphate-Co $B_6$ | 0.6 | 5 | P-5-P monohydrate |
| Selenomethionine (0.5%) | 0.5 | 4 | L-selenomethionine |
| Vitamin A Palmitate (500,000 IU/GR) | 0.5 | 4 | |
| Copper Sebacate (14%) | 0.4 | 2.9 | |
| Red beet root powder | 6.1 | 50 | Beta vulgaris rubra |
| Stearic acid | 1.5 | 12 | |
| Sorbitol | 1.3 | 11 | |
| Acdisol | 0.4 | 3 | Microcrystalline cellulose |
| Coconut oil | 0.1 | 1 | Magnesium stearate |
| Syloid | 0.1 | 1 | Silicon dioxide (amorphous) |
| Total | 820.7 | 100 | |

These tablets are an example of one embodiment of a unit dose according to the present invention.

Examples 4–7

TESTING OF THE PRODUCT

The tablets of Example 3 were administered to test 73 female subjects to determine the effects on the elasticity, firmness, and presence of fine lines and wrinkles of the skin. A seven day conditioning period was used prior to initiation of the study, where subjects were instructed to discontinue use of all moisturizing products, sun screens and liquid make-ups, and to avoid excessive UV exposure and tanning salons. Subjects were permitted to use their current eye, powder blush, and lip products, and non-moisturizing soap.

Test subjects not in the control group, which consumed placebo tablets, consumed two (2) tablets of the test material of Example 3 daily with meals. Before, and after two (2) and five (5) weeks of tablet use, the subjects were measured as described below. Before measurements were taken, all subjects were allowed to equilibrate for thirty minutes at approximately 68° F. and 44 percent relative humidity. At each measurement phase, three Comeometer readings, a negative impression using Silflo replicating material, and three Ballistometer and Cutometer readings were made on the test sites indicated below.

A total of 65 subjects completed the study, as 7 discontinued the study for unrelated reasons and 1 developed a rash for 5 days. There were 12 subjects in the control group and 53 using the tablets.

Example 4

Image Analysis

The texture of the skin, fine lines, and wrinkles were assessed by taking Silflo replicas of the periorbital area (crow's feet) at each of the three test times. These negative impressions, or Silflo replicas, were illuminated at a precisely defined angle of 35° to create shadows for analysis by shades of gray. The skin topography is defined by the: (a) number of wrinkles; (b) total area of wrinkles; (c) total length of wrinkles; (d) mean length of wrinkles; and (e) mean depth of wrinkles. The type of wrinkles was determined on the basis of depth, length, and area.

As indicated in Table I below, the number of wrinkles were significantly reduced by 34 percent ($p<0.01$) and the number of fine lines by 34 percent $p<0.06$) as a result of 5 weeks using the test material.

TABLE I

| | Number of Wrinkles and Fine Lines | | | | | | | |
|---|---|---|---|---|---|---|---|---|
| | Number of Wrinkles | | | | Number of Fine Lines | | | |
| | Mid-Baseline | | Final-Baseline | | Mid-Baseline | | Final-Baseline | |
| | Control | Treated | Control | Treated | Control | Treated | Control | Treated |
| Average | −3 | −7 | −3 | −15 | −5 | −4 | −6 | −12 |
| Standard Deviation | 9 | 13 | 13 | 12 | 6 | 10 | 14 | 10 |
| p value | $p < 0.41$ | | $p < 0.01$ | | $p < 0.96$ | | $p < 0.06$ | |
| % Difference from Baseline | −11% | −19% | −6% | −40% | −14% | −24% | −9% | −43% |
| Total % Difference (T − C) | −8% | | −34% | | −10% | | −34% | |

T = Treated
C = Control

Example 4 indicates that use of tablets prepared according to the invention result in a 10 percent decrease in appearance of wrinkles and an 8 percent decrease in fine lines after only 2 weeks of treatment, and a decrease of 34 percent in both wrinkles and fine lines after 5 weeks. Additionally, the observed degree of improvement is a function of the length of treatment as indicated above. This strongly suggests the treatment has imparted an improved skin infrastructure by beneficially affecting the dermis of the skin.

Example 5

Ballistometer

The Ballistometer is an instrument designed to evaluate in vivo, in a non-invasive manner, the viscoelastic properties of the skin. It analyzes the bounce pattern displayed by a probe that is allowed to impact on the skin. The kinetic energy of the probe striking the skin is stored by the elastic components of the skin and released back to make the probe rebound to a lower height. The height to which the probe will rebound depends upon the amount of stored energy lost in shear viscosity within the skin.

The capacity of the skin to absorb mechanical energy may thus be measured. Although it is unclear exactly which layer, or layers, of the skin are responsible, the mechanical properties of the dermis/epidermis layers are controlled by the density and geometry of the network of collagen fibers. It is believed the Ballistometer describes mostly the tissues underlying the stratum corneum.

Tests were conducted with the Ballistometer on one randomly chosen side of the face, slightly below the cheek bone area. The height of first rebound and the coefficient of restitution ("COR") were measured. The COR is the ratio of the first to the second rebound. Table II, below, indicates that the COR decreases by 10 percent ($p<0.11$) and the height of the first rebound reduced by 18 percent ($p<0.02$) as a result of 5 weeks use of the product. This indicates that less of the energy of the striking probe was restored, thus, a greater amount of energy was dissipated in the skin. This suggests the skin became softer and more yielding during the test period.

TABLE II

| | Ballistometer Readings | | | | | | | |
|---|---|---|---|---|---|---|---|---|
| | Height of First Rebound (mm) | | | | Coefficient of Restitution | | | |
| | Mid-Baseline | | Final-Baseline | | Mid-Baseline | | Final-Baseline | |
| | Control | Treated | Control | Treated | Control | Treated | Control | Treated |
| Average | −0.16 | −0.06 | 0.49 | 0.06 | −0.02 | 0.00 | 0.01 | 0.00 |
| Standard Deviation | 0.41 | 0.48 | 0.52 | 0.51 | 0.03 | 0.02 | 0.03 | 0.03 |
| p value | $p < 0.56$ | | $p < 0.02$ | | $p < 0.06$ | | $p < 0.11$ | |
| % Difference from Baseline | −6% | 0% | 22% | 4% | −12% | −0% | 12% | 2% |
| Total % Difference (T − C) | 6% | | −18% | | 12% | | −10% | |

T = Treated
C = Control

Example 6

Cutometer

The Cutometer is a commercially available instrument (Courage & Khazaka, Germany) designed to measure the mechanical properties of the skin in a non-invasive manner. It measures the vertical deformation of the skin's surface when pulled by vacuum suction (500 mm Hg) through the small aperture (2 mm) of a probe and the depth of penetration of the skin into the probe optically with an accuracy of 0.01 mm. The probe is attached to a computer, which completely controls probe operation and plots skin deformation as a function of time. From this curve, a number of variables can be extrapolated to estimate the elastic, viscoelastic, and purely viscous behavior of the skin.

The following parameters were recorded: (a) the immediate distension ($U_e$), measured at 0.1 seconds; (b) the delayed distension ($U_v$); (c) the final distension ($U_f$), measured at 10 seconds; and (d) immediate retraction ($U_r$). The deformation parameters are extrinsic parameters dependent on skin thickness, and a variety of biologically important ratios were calculated: (a) $U_r/U_f$, a measure of net elasticity of the skin; (b) $U_r/U_e$, the biological elasticity, or measurement of the ability of the skin to regain its initial configuration after deformation; and (c) $U_v/U_e$ the viscoelastic to elastic ratio, where an increase in this ratio indicates and increase in the viscoelastic portion of the deformation and/or a relative decrease of the elastic portion.

Tests were conducted using a Cutometer on both sides of the face on the cheek area. Table m, below, indicates that the delayed distension ($U_v$) decreased a significant 16 percent ($p<0.04$) after 5 weeks of treatment. This parameter reflects viscoelastic properties of the skin and, thus, the behavior of the dermis. After 5 weeks, there were no statistically significant changes in $U_e$, the immediate distension, which is primarily affected by the moisture content and mechanical properties of the stratum corneum.

TABLE III

| | Cutometer Readings | | | | | | | |
|---|---|---|---|---|---|---|---|---|
| | $U_f$ (mm) | | | | $U_e$ (mm) | | | |
| | Mid-Baseline | | Final-Baseline | | Mid-Baseline | | Final-Baseline | |
| | Control | Treated | Control | Treated | Control | Treated | Control | Treated |
| Average | 0.071 | 0.040 | 0.026 | 0.020 | 0.046 | 0.021 | 0.008 | 0.009 |
| Standard Deviation | 0.038 | 0.058 | 0.058 | 0.049 | 0.028 | 0.042 | 0.048 | 0.043 |
| p value | $p < 0.11$ | | $p < 0.71$ | | $p < 0.08$ | | $p < 0.96$ | |
| % Difference from Baseline | 39% | 20% | 16% | 11% | 36% | 16% | 11% | 10% |
| Total % Difference (T − C) | −19% | | −5% | | −20% | | −1% | |
| | $U_v$ (mm) | | | | $U_r$ (mm) | | | |
| | Mid-Baseline | | Final-Baseline | | Mid-Baseline | | Final-Baseline | |
| | Control | Treated | Control | Treated | Control | Treated | Control | Treated |
| Average | 0.026 | 0.020 | 0.018 | 0.010 | 0.033 | 0.017 | 0.013 | 0.008 |
| Standard Deviation | 0.015 | 0.018 | 0.015 | 0.011 | 0.018 | 0.027 | 0.030 | 0.023 |
| p value | $p < 0.27$ | | $p < 0.04$ | | $p < 0.09$ | | $p < 0.55$ | |
| % Difference from Baseline | 51% | 39% | 34% | 19% | 48% | 26% | 19% | 15% |
| Total % Difference (T − C) | −12% | | −16% | | −22% | | −5% | |

TABLE III-continued

Cutometer Readings

| | $U_r/U_e$ | | | | $U_v/U_e$ | | | |
|---|---|---|---|---|---|---|---|---|
| | Mid-Baseline | | Final-Baseline | | Mid-Baseline | | Final-Baseline | |
| | Control | Treated | Control | Treated | Control | Treated | Control | Treated |
| Average | 0.004 | 0.034 | 0.042 | 0.027 | 0.017 | 0.063 | 0.092 | 0.048 |
| Standard Deviation | 0.105 | 0.064 | 0.062 | 0.064 | 0.073 | 0.078 | 0.132 | 0.073 |
| p value | $p < 0.21$ | | $p < 0.45$ | | $p < 0.08$ | | $p < 0.13$ | |
| % Difference from Baseline | 2% | 7% | 9% | 6% | 8% | 19% | 28% | 16% |
| Total % Difference (T − C) | 5% | | −3% | | 12% | | −12% | |

| | $U_r/U_f$ | | | |
|---|---|---|---|---|
| | Mid-Baseline | | Final-Baseline | |
| | Control | Treated | Control | Treated |
| Average | 0.024 | 0.014 | 0.012 | 0.003 |
| Standard Deviation | 0.034 | 0.040 | 0.036 | 0.037 |
| p value | $p < 0.47$ | | $p < 0\ 0.46$ | |
| % Difference from Baseline | 6% | 4% | 3% | 1% |
| Total % Difference (T − C) | −2% | | −2% | |

T = Treated
C = Control

Example 7

Corneometer

The general appearance of soft, smooth skin depends largely on the presence of an adequate amount of water in the stratum corneum. The Comeometer is a commercially available instrument (Courage & Khazaka, Germany) to measure the changes in capacitance of the skin resulting from changes in the degree of hydration. It is particularly sensitive to low levels of hydration, and uses measurements of arbitrary units of skin hydration (H) to express capacitance.

Tests were conducted using a Comeometer on both sides of the face on the cheek area. Changes in moisture content of the stratum corneum occur rapidly due to changes in the environment, including hydration from the use of moisturizing agents and humectants. Thus, the measurements with the Ballistometer and Cutometer indicate changes occurred in deeper layers of the skin, rather than the superficial stratum corneum. Table IV shows no significant changes in the hydration of the stratum corneum following 2 weeks ($p<0.84$) and 5 weeks ($p<0.67$) of product use.

TABLE IV

Corneometer Readings

| | Skin Hydration (H) | | | |
|---|---|---|---|---|
| | Mid-Baseline | | Final-Baseline | |
| | Control | Treated | Control | Treated |
| Average | −5 | −7 | −8 | −4 |
| Standard Deviation | 6 | 7 | 5 | 7 |
| p value | < 0.84 | | $p < 67$ | |
| % Difference from Baseline | −7% | −10% | −12% | −6% |
| Total % Difference (T − C) | −3% | | 6% | |

T = Treated
C = Control

Examples 8–10

Testing of Various Embodiments of the Invention

The effectiveness of an orally ingested product according to the invention was tested for its ability to reduce the appearance of cellulite in the thigh area. A total of eighteen (18) female subjects ranging in age from 32 to 65 years of age were selected to evaluate the composition of the invention. Al subjects exhibited visible signs of moderate or greater cellulite (Grade 2 or higher); had the absence of any visible skin disease(s) which might be confused with a skin reaction from the test material; were in general good health with no known allergies, especially to cosmetic or toiletry products; had no evidence of acute or chronic disease; had completed a medical history form, as well as understood and signed an Informed Consent form; were dependable and capable of following directions; were not pregnant or lactating; were not on any diet or weight reduction program; and were not on any regular exercise program (immediately prior to or during the course of the study).

At baseline, each subject received a visual examination conducted by a qualified technician, and had a skin replica made of the area considered most representative of the overall appearance of cellulite. Subjects were tested on the right or left thigh. The test sites were carefully demarcated to ensure subsequent evaluations were made on the same test areas. The test sites were examined by a trained observer and scored for the degree of cellulite at each clinic visit according to the following scale:

0=No visible cellulite
1=Very little visible cellulite, no dimpling
2=Visible cellulite, evidence of shallow dimpling
3=Easily visible cellulite, moderate to pronounced dimpling
4=Extremely visible cellulite, heavy and deep dimpling
Note: Half-point increments could be used to better define observed levels of cellulite.

Replicas were completed with the subject in a standing position. Silicone replicas (2 cm×5 cm) were obtained at the baseline and week 6 using the following materials: Silflo® Silicone impression material, (commercially available from Flexico, of England), Silflo® Universal Accelerator, weighing boat, and spatula.

The panel was divided into two groups, nine (9) subjects per group. The first group, Group A, took two (2) Youth Builder™ supplements, twice daily, preferably with meals (morning and evenings). The second group, Group B, took two (2) Youth Builder™ supplements, preferably with meals (morning and evenings) and one (1) Garcinia tablet twice daily, preferably with meals (morning and evenings).

The Youth Builder™ supplements (commercially available from Murad Inc., of El Segundo, Calif.) contained the following ingredients:

| Ingredient | Percent (w/w) |
| --- | --- |
| Vitamin A (palmitate) | 0.33 |
| Niacinamide | 1.67 |
| Vitamin B-6 (from pyrodoxine HCL) | 0.42 |
| Vitamin C (from magnesium ascorbate) | 8.33 |
| Vitamin E (d-alpha tocopheryl succinate) | 1.75 |
| N-acertyl D-glucosamine | 3.33 |
| L-proline | 7.5 |
| L-lysine (HCL) | 6.67 |
| Glucosamine sulfate | 11.7 |
| N-acetyl cysteine | 3.33 |
| Quercetin | 2.50 |
| Grape seed extract (38.4%) | 1.67 |
| Zinc (Opti-Zinc) | 0.63 |
| Manganese (ascorbate) | 2.50 |
| Copper (sebacate) | 0.70 |
| Selenomethionine (L-selenomethionine) | 0.08 |
| Beet root powder | 0.01 |
| Dicalcium phosphate | 15.6 |
| Microcrystalline cellulose | 1.67 |
| Stearic acid | 23.3 |
| Magnesium stearate | 1 |
| Silica | 1 |
| Croscarmellose sodium | 4.2 |
| Talc | 0.21 |
| Pharmaceutical glaze | |

The Garcinia tablets, 365 Murad™, (commercially available from Murad, Inc., of El Segundo Calif.) contained citrin® (*garcinia cambogia*, 2000 mg (yielding 100 mg of (−) hydroxycitric acid as calcium hydroxycitrate), 200 mg L-phenylalanine, and 200 mg chromium.

Subjects were provided with a three (3) week supply of their randomly assigned test product(s) for use at home and were instructed to discontinue the use of their normal anti-cellulite products, to avoid introducing any new products for treating cellulite during the study, and to not be on any diet or weight reduction program or on any regular exercise program immediately prior to or during the course of the study. Each subject was also instructed to keep a diary to document compliance. After three weeks of product usage, the subjects returned to the laboratory for a visual evaluation of the test sites. Another three (3) week supply of their assigned test product(s) and a new diary was then dispensed to each subject. After the second three (3) weeks of product usage (week 6), the subjects returned to the laboratory for a final visual evaluation and to have another skin replica of the test site taken. All diaries were reviewed for compliance.

Seventeen (17) subjects completed the evaluation. The remaining subject discontinued participation due to personal reasons unrelated to product usage. During the study five (5) patients reported minor adverse events such as itching and/or redness, stomach cramps, diarrhea, and constipation. None of the adverse events were serious enough to cause a subject to discontinue the study.

Statistical Analysis of the data was performed using repeated measures ANOVA to determine if any significant (P <0.05) differences were observed between the baseline, the 3 week, and the 6 week post-treatment scoring intervals. Repeated measures ANOVA and dependent t-test were performed using ThinkPoint™ Statistics Menu V.5, for Microsoft Excel V.5 or later (commercially available from ThinkPoint™ Statistics Menu, LLC, Sandy, Utah). If significance was observed, the t-Test (Dependent) was used to compare individual columns of data.

Example 8

Visual Assessment

Visually-assigned individual cellulite scores were assessed. For Group A (Youth Builder™ supplements alone), one in eight subjects (1/8, 12.5%) exhibited improvement in visually scored cellulite at the 3 week post treatment scoring interval and three of eight subjects (3/8, 37.5%) exhibited improvement at the 6 week post treatment scoring interval when compared to baseline.

For Group B (Youth Builder™ supplements and Garcinia), three of nine subjects (3/9, 33.3%) exhibited improvement in visually scored cellulite at the 3 week post treatment scoring interval and six of nine subjects (6/9, 67.7%) exhibited improvement at the 6 week post treatment scoring interval when compared to baseline.

Although there was a small number of test subjects, certain trends are evident from the statistical analysis. For subjects taking Youth Builder™ supplements alone (Group A) the overall improvements in visually scored cellulite were not significant at P<0.05, but exhibited marginal significance at P<0.089 (Repeated Measures Analysis of Variance). For subjects taking Youth Builder™ supplements and garcinia, repeated measures ANOVA indicated that highly significant ($P \leq 0.008$) improvements in visually scored cellulite were obtained between baseline and/or the 3 week and 6 week post treatment scoring intervals. t-Test (Dependent) analyses showed marginal significance ($P \leq 0.081$) between baseline and week 3 but highly significant ($P \leq 0.008$) improvements between baseline and week 6.

Example 9

Skin Unevenness

The replicas of the 17 subjects who completed the study were analyzed. A skin surface contour analysis was performed on the replicas. The skin contour analysis was performed with an IBM compatible Pentium III 500 Mhz personal computer with a math co-processor and 128 mb memory running under Windows 98; and a SONY solid state B&W video camera with a 50 mm lens/5 mm extension, ITI OFG frame grabber, and SONY Trinitron monitor. The computer was equipped with OPTIMAS v6.2, Microsoft EXCEL 2000, and StatSoft STATISTICA 5.5 software. Illumination was provided by a structured laser light source consisting of parallel lines projected at 45 degrees from the plane of the replica surface.

The skin contour replica analysis was performed by taking a replica of the thigh surface with Siflo® silastic resin using a specialized frame to orient and support the replica on the skin. The resulting replica is approximately 2 cm by 5 cm. Skin surface elevation or contour, as sampled by the replica, was then determined and the degree of variation of the elevation over the sampled surface was analyzed. The replica surface elevation is measured by the displacement of a projected array of laser light lines spaced at intervals over the replica surface. When viewed from above, the image of the lines on the replica appear dispaced from the reference positions in proportion to the contour height of the replica surface.

For the 2 cm by 5 cm replica, five (5) equally spaced laser lines were projected and analyzed. The image analyzer was programmed to determine the location of each displaced projected line at 10 equally spaced locations along the length of the laser line. The displacement (difference between the positions measured for a planar reference and positions measured for the replica sample) was calculated for each of 50 sampling points. The data for each replica constituted a map of the surface elevation at 50 points on the surface. The data was recorded in a raw data file as the spacing parameter. The standard deviation of the elevations was computed as a measure of the unevenness of the surface. To overcome contributions from a general tilt of the replica surface, which does not contribute to the unevenness of the surface, the spacing data was fit to a hypothetical flat surface and the differences between the hypothetical reference surface and the observed map elevations was computed. The standard deviation of these differences called the Standard Deviation of the Residuals (RSTD) is a measure of the unevenness of the contour surface independent of any overall tilt in the replica surface. The unit of measure for the RSTD is millimeters. The RSTD value was recorded in the results file and constituted the main reported datum for the replica.

The following parameters are reported for the skin contour analysis:

SPSTD: Standard deviation of spacing shift, which measures the variation of the surface including overall shape contribution. The smaller the SPSTD the smoother the surface of the skin.

RSTD: Standard deviation of the residuals. The smaller the RSTD the smoother the surface of the skin.

NLARGE: The number of points falling more than a standard deviation above or below the fitted surface. The smaller the NLARGE the smoother the surface of the skin.

Replicas taken from subjects at baseline ($T_0$) and after the final visit ($T_1$) were compared.

Changes from baseline were calculated by subtracting the baseline values for each subjects from the final values. The mean changes were tested for significance using the one sample t-test against a value of zero.

$t=\sqrt{n}\cdot(mean-u_0)/std.dev.$ where $u_0=0$.

The t statistic was compared with values of the t distribution for the known degrees of freedom, n−1.

The data showed statistically significant changes (p<0.05) from baseline for all 3 parameters for group A but not group B. The combined groups also exhibited statistically significant changes for the SPSTD and RSTD parameters but not the NLARGE parameter. The results for groups A and B were also compared using the t-Test for independent groups. While the trend was in the direction of A being more improved than B, the differences were not statistically significant.

Overall, significant improvements in skin unevenness parameters were found for Group A and for the two groups combined.

Example 10

Skin Texture, Roughness and Wrinkles

The same replicas were also examined for changes in fine texture in the center portion of the 2×5 cm sample. In these replicas, the fine lines run in the long dimension of the sample so the texture assay was made with lighting directed normal to the long dimension. Skin contour analysis for wrinkle texture parameters were performed with an IBM compatible Pentium III 500 Mhz personal computer with a math co-processor and 128 mb memory running Windows 98 and a Cohu Solid State B&W video camera with a 50 mm lens/30 mm extension, ITI OFG frame grabber and SONY Trinitron monitor. The computer was equipped with OPTIMAS v6.2, Microsoft EXCEL 2000, and StatSoft STATISTICA 5.5 software. Illumination was obtained using a collimated light source directed at a 25 angle from the plane of the replica.

The general background gradient of light intensity was adjusted by applying a $2^{nd}$ order correction in the direction of the light propagation. The shadow texture produced by the oblique lighting of the negative replica was analyzed by two types of assay methods (A and B).

Method A: The luminance was measured along a set of 10 equal length parallel lines (passes) running across the replica parallel to the lighting direction. The variations in luminance (lightness/darkness) were treated as indicative of the roughness and analyzed by the following traditional surface roughness statistics:

Rz: The average maximum difference in luminance value for five equal length segments in each of the 10 lines traversing the sample. The Rz value measures the maximal optical roughness.

Ra: The average deviation of the luminance cure about the mean luminance for the same 10 lines. The Ra value measures the average optical roughness.

The Rz and Ra parameter are reported in the units of brightness (gray levels) ranging from 0 to 255.

Fspace: Measures the distance between markers placed on the lines at luminance changes indicative of fine line spacing (mm).

Fnum: Is the number of fine line markers (per mm).

Method B: The replica image area is divided into 10 equal width bands or sub-areas. Shadow like features are detected in each of these bands according to their luminance values being less than the detection threshold (Threshold Algorithm: Cutoff=that gray level halfway between black and the most probable gray value in the image. The most probable gray value typically characterizes the flat, featureless regions of the replica. Shadows–100.0* sum (ArROIHistogram[Lo..(CUTOFF+1)])/totalpixels). Four parameters were determined from the detected features.

Spacing: The mean distance in millimeters between adjacent detected features (i.e., the spacing between the midpoints of adjacent shadowy features).

Breadth: The average breadth of the detected features in millimeters. This parameter is proportional to the depth of the wrinkle producing the shadow.

Shadows: The percent of the sampled replica area with luminance values less than the detection threshold. This is the relative area of shadows cast by the wrinkles and fine lines in the replica.

Num Wrinkles: The total number of features detected in the 10 bands or sub-areas used to calculate spacing and breadth.

Statistically significant changes were found for Fspace, Fnum, Spacing, and Num Wrinkle parameters. The significant changes more often involved group A than group B. The combined groups also exhibited statistically significant changes in these 4 parameters. Overall, the results suggest a tighter, more compact texture as a result of treatment, especially for group A.

The results of Examples 8–10 show that significant improvements in the skin unevenness parameters were found for Group A (Youth BuilderTM supplements alone) and for both groups (A and B) combined. The results of the texture analysis suggest a tighter, more compact texture as a result of treatment, especially for Youth Builder™ supplements alone. The results of the study show significant or near significant improvements in visibly scored cellulite are obtained for both Youth Builder™ supplements alone (more pronounced using skin image analysis) and for Youth Builder™ supplements plus Garcinia (more pronounced using visual scoring of cellulite levels).

Various modifications of the invention in addition to those shown and described herein will be apparent to those skilled in the art from the foregoing description. Such modifications are also intended to fall within the scope of the appended claims. The foregoing disclosure includes all the information deemed essential to enable those skilled in the art to practice the claimed invention.

What is claimed is:

1. A pharmaceutical composition for reducing or eliminating the appearance of cellulite in a patient comprising:
   a sugar compound that is converted to a glycosaminoglycan in the patient in an amount sufficient to thicken the skin;
   a primary antioxidant component in an amount sufficient to substantially inhibit the activity of collagenase and elastase;
   at least one amino acid component in an amount sufficient to assist in the thickening of the skin;
   at least one transition metal component in an amount effective to bind collagen and elastic fibers and thicken the skin;
   at least one of either a fat burner to reduce absorption of fat in the digestive tract or prevent the production of fat, or a vascular dilator to improve blood supply to the skin; and
   chromium picolinate in an amount sufficient to facilitate entry of sugar into the cells to improve metabolism of fats by the body.

2. The composition of claim 1 wherein a fat burner is present.

3. The composition of claim 1 wherein a vascular dilator is present.

4. The composition of claim 1, wherein the sugar compound is present in an amount of from about 5 to 50 weight percent of the composition, the primary antioxidant component is present in an amount of about 5 to 50 weight percent of the composition, the amino acid component is present in an amount of about 8 to 60 weight percent of the composition, and the transition metal component is present in an amount of about 0.5 to 15 weight percent of the composition.

5. The composition of claim 1, wherein the sugar compound is N-acetylglucosamine, or a pharmaceutically acceptable salt or ester thereof.

6. The composition of claim 5, wherein the N-acetylglucosamine, or a pharmaceutically acceptable salt or ester thereof, is present in an amount of about 5 to 30 weight percent of the composition.

7. The composition of claim 1, wherein the anti-oxidant is a vitamin C source.

8. The composition of claim 7, wherein the vitamin C source is present in an amount of about 5 to 50 weight percent of the composition.

9. The composition of claim 1, wherein the amino acids are selected from lysine, proline, cysteins, glycine, methionine, or mixtures thereof.

10. The composition of claim 9, wherein the amino acids are each present in an amount of about 2 to 25 weight percent of the composition.

11. The composition of claim 1, wherein the transition metal is one or more of zinc, manganese, or copper.

12. The composition of claim 11, wherein the zinc, if present, is present in an amount of about 1 to 10 weight percent of the composition; the manganese, if present, is present in an amount of about 1 to 10 weight percent of the composition; and the copper, if present, is present in an amount of about 0.1 to 5 weight percent of the composition.

13. The composition of claim 1, further comprising a proanthanol or proanthocyanidin.

14. The composition of claim 13, wherein the proanthanol or proanthocyanidin is present in an amount of 0.5 to 5 weight percent of the composition.

15. The composition of claim 3, wherein the vascular dilator is one or more of an extract of ginko biloba, a ginsing extract, or phenylalanine.

16. The composition of claim 2, wherein the fat burner is hydroxy acetic acid or chitin.

* * * * *